United States Patent [19]

Van Tassel et al.

[11] Patent Number: 6,042,634
[45] Date of Patent: Mar. 28, 2000

[54] MOISTURE EXTRACTOR SYSTEM FOR GAS SAMPLING

[75] Inventors: Norman L. Van Tassel, Pittsburgh; William J. Perroz, Jr., North Vandergrift; Richard M. Hickox, Pittsburgh, all of Pa.

[73] Assignee: Bacharach, Inc., Pittsburgh, Pa.

[21] Appl. No.: 09/064,419

[22] Filed: Apr. 22, 1998

[51] Int. Cl.[7] .......................... B01D 53/04; B01D 53/22; B01D 53/26

[52] U.S. Cl. ..................... 95/14; 95/18; 95/25; 95/52; 95/117; 96/10; 96/112; 96/117; 96/413; 96/420

[58] Field of Search ....................... 95/10, 14, 18, 95/25, 45, 52, 117–120; 96/108, 112, 115, 117, 4, 413, 10, 417, 420, FOR 170, FOR 171

[56] References Cited

U.S. PATENT DOCUMENTS

| | | | |
|---|---|---|---|
| 3,241,293 | 3/1966 | Pfefferle | 96/4 X |
| 3,367,850 | 2/1968 | Johnson | 95/52 X |
| 3,545,931 | 12/1970 | McKinley, Jr. | 96/10 X |
| 3,604,246 | 9/1971 | Toren | 95/52 X |
| 3,674,435 | 7/1972 | VanLuik, Jr. et al. | 96/4 X |
| 3,680,388 | 8/1972 | Critchley et al. | 73/421.5 R |
| 3,735,558 | 5/1973 | Skarstrom et al. | 55/16 |
| 3,923,461 | 12/1975 | Barden | 96/4 X |
| 3,926,561 | 12/1975 | Lucero | 95/45 X |
| 4,293,316 | 10/1981 | Block | 96/4 X |
| 4,459,040 | 7/1984 | Vories | 374/31 |
| 4,497,640 | 2/1985 | Fournié et al. | 95/10 |
| 4,705,543 | 11/1987 | Kertzman | 55/158 |
| 4,793,830 | 12/1988 | Murphy et al. | 95/52 X |
| 4,808,201 | 2/1989 | Kertzmann | 55/158 |
| 4,886,528 | 12/1989 | Aaltonen et al. | 96/10 X |
| 5,002,590 | 3/1991 | Friesen et al. | 95/52 |
| 5,226,932 | 7/1993 | Prasad | 95/45 |
| 5,240,486 | 8/1993 | Springman et al. | 55/320 |
| 5,649,995 | 7/1997 | Gast, Jr. | 96/10 X |

FOREIGN PATENT DOCUMENTS 2308988  7/1997  United Kingdom .

OTHER PUBLICATIONS

Japanese Abstract No. JP9094425, published Apr. 8, 1997.

*Primary Examiner*—Robert H. Spitzer
*Attorney, Agent, or Firm*—Webb Ziesenheim Logsdon Orkin & Hanson, P.C.

[57] ABSTRACT

A gas sampling apparatus includes a probe tube having a tip positionable in a stream of products of combustion and a sample dryer tube connected in fluid communication with an end of the probe tube opposite the tip. The sample dryer tube is received in a purge gas tube along a lengthwise axis thereof. The purge gas tube and the sample dryer tube define therebetween a space through which a purge gas pump urges a purge gas in a first direction. A sample pump connected in fluid communication with the sample dryer tube urges therethrough in a second direction opposite the first direction a sample of gas obtained from the stream of products of combustion via the probe tube. A sensor is positioned to detect a constituent of the sample of gas exhausted from the sample dryer tube. The sample dryer tube is formed at least in part of a hydrophilic membrane and the purge gas entering the space contains less water vapor than the sample of gas. Water vapor contained in the sample of gas is conveyed through the hydrophilic membrane part of the sample dryer tube to the purge gas flowing in the space so that the purge gas exhausted from the space contains more water vapor than the purge gas entering the space and the sample of gas exhausted from the sample dryer tube contains less water vapor than the sample of gas entering the sample dryer tube.

20 Claims, 5 Drawing Sheets

MOISTURE EXTRACTOR SYSTEM FOR GAS SAMPLING

BACKGROUND OF THE INVENTION

1. Field of the Invention

This invention relates to a method and apparatus for sampling a gas from a stream of products of combustion and, more particularly, for removing water from a gas sample.

2. Description of the Prior Art

The combustion of a fuel and an oxidizer produces products of combustion which include constituents such as $NO_2$ and $SO_2$. Moreover, $H_2O$ in the form of water vapor is also produced during combustion. It is desirable when analyzing emissions of a combustion process to measure from a sample of the products of combustion one or more of the constituents. However, the water vapor condensing in the sample of the products of combustion absorbs some of the constituents to be detected, thereby affecting the accuracy of measurement.

To reduce the absorption of constituents by the water vapor condensing in the sample of the products of combustion, prior art combustion analyzers direct the heated sample of the products of combustion across a "cold plate" positioned between a stream of products of combustion flowing in an exhaust stack and one or more electrochemical sensors, each adapted to detect one or more constituents in the sample of the products of combustion. In theory, when the sample of the products of combustion contacts or passes adjacent the cold plate, the water vapor contained in the sample condenses onto the cold plate. The condensed water vapor then flows to a water trap remote from the cold plate. In practice, however, the cold plate does not precipitate water vapor from the sample of the products of combustion at a sufficient rate to avoid some interference with the measurement of one or more constituents therein. More specifically, the cold plate is formed from a Peltier junction. When exposed to the heated sample of products of combustion, the Peltier junction increases in temperature thereby reducing the ability of the cold plate to precipitate water vapor from the sample of products of combustion. Moreover, Peltier junctions are inefficient, thus requiring a large power supply to provide electrical power thereto.

It is, therefore, an object of the present invention to provide a method and apparatus for extracting water vapor from the sample of the products of combustion more thoroughly than prior art gas sampling systems. It is an object of the present invention to provide to an electrochemical sensor of a combustion analyzer the sample of the products of combustion, having the water vapor removed therefrom, at a temperature within a desired range of operating temperatures for the electrochemical sensor. Still further objects will become apparent to those of ordinary skill in the art upon reading and understanding the following detailed description.

SUMMARY OF THE INVENTION

Accordingly, we have invented an apparatus for obtaining a sample of gas from a stream of products of combustion. The apparatus includes a probe tube having a tip positionable in the stream of products of combustion. A sample dryer tube is connected in fluid communication with an end of the probe tube opposite the tip. The sample dryer tube is received in a purge gas tube along a lengthwise axis thereof and the purge gas tube and the sample dryer tube form a space therebetween. A source of purge gas urges purge gas through the space in a first direction. A sample pump connected in fluid communication with the sample dryer tube urges in a second direction opposite the first direction the sample of gas obtained from the stream of products of combustion via the probe tube. A sensor is positioned to detect a constituent in the sample of gas exhausted from the sample dryer tube. The purge gas entering the space contains less water vapor than the sample of gas entering the sample dryer tube. The sample dryer tube is formed at least in part of a hydrophilic membrane. Water vapor contained in the sample of gas is conveyed through the hydrophilic membrane part of the sample dryer tube to the purge gas flowing in the space so that the purge gas exhausted from the space contains more water vapor than the purge gas entering the space, and the sample of gas exhausted from the sample dryer tube contains less water vapor than the sample of gas entering the sample dryer tube.

A probe tube heater can be positioned adjacent the tip of the probe tube for maintaining the temperature of the sample of gas received in the probe tube above the dew point temperature of water vapor therein. A temperature probe can be positioned on the probe tube for detecting a temperature thereof. The temperature probe has an output that varies as a function of the detected temperature. A temperature controller has an input connected to the temperature probe for detecting the output thereof and has an output connected to the probe tube heater for supplying electrical power to the probe tube heater as a function of the output of the temperature probe detected by the temperature controller. Alternatively, the temperature probe is eliminated and the temperature controller detects a resistance of the probe tube heater and supplies electrical power thereto as a function of the detected resistance.

A purge gas tube heater can be positioned adjacent the purge gas tube for maintaining the temperature of the sample of gas received in the sample dryer tube above the dew point temperature of water vapor therein. A temperature sensitive switch is electrically connected between the purge gas tube heater and a source of electrical power and is positioned to detect the temperature of the purge gas tube heater. The switch causes electrical power to be supplied to the purge gas tube heater as a function of the temperature detected thereby.

The source of purge gas can include a dryer and a purge gas pump connected in series with the space, a bottle of dry purge gas, or a freezing dryer. The dryer can include a container having a desiccant received therein. The purge gas pump urges the purge gas, preferably ambient air, through the desiccant which removes the water vapor therefrom. Preferably, the sample of gas exhausted from the sample dryer tube has a dew point temperature below 50° F. and the flow rate of the purge gas is at least twice the flow rate of the sample of gas. More specifically, the flow rate of the purge gas is preferably greater than the product of the flow rate of the sample of gas and the percentage of water vapor in the sample of gas divided by the dew point moisture capacity of the purge gas.

We have also invented a method of sampling gas obtained from a stream of products of combustion. The method includes obtaining a sample of gas from the stream of products of combustion. The sample of gas is urged through a sample dryer tube disposed inside a purge gas tube. A purge gas is urged through a space formed between the purge gas tube and the sample dryer tube in a direction opposite the sample of gas in the sample dryer tube. The sample dryer tube adjacent an end thereof which receives a sample of gas therein is maintained at or above a temperature above the dew point temperature of water in the sample of gas. A constituent in the sample of gas exhausted from the sample dryer tube is sensed. The purge gas entering the space contains less water vapor than the sample of gas entering the sample dryer tube. The sample dryer tube is formed at least in part from a hydrophilic membrane which enables water vapor to be conveyed from the sample of gas to the purge gas whereby the purge gas exhausted from the space contains more water vapor than the purge gas entering the space, and the sample of gas exhausted from the sample dryer tube contains less water vapor than the sample of gas entering the sample dryer tube.

The sample of gas in advance of entering the sample dryer tube can be maintained at a temperature above the dew point temperature of water therein. Heat is withheld from the end of the sample dryer tube adjacent the end thereof where the sample of gas is exhausted.

DETAILED DESCRIPTION OF THE PREFERRED EMBODIMENT

Figure 1:
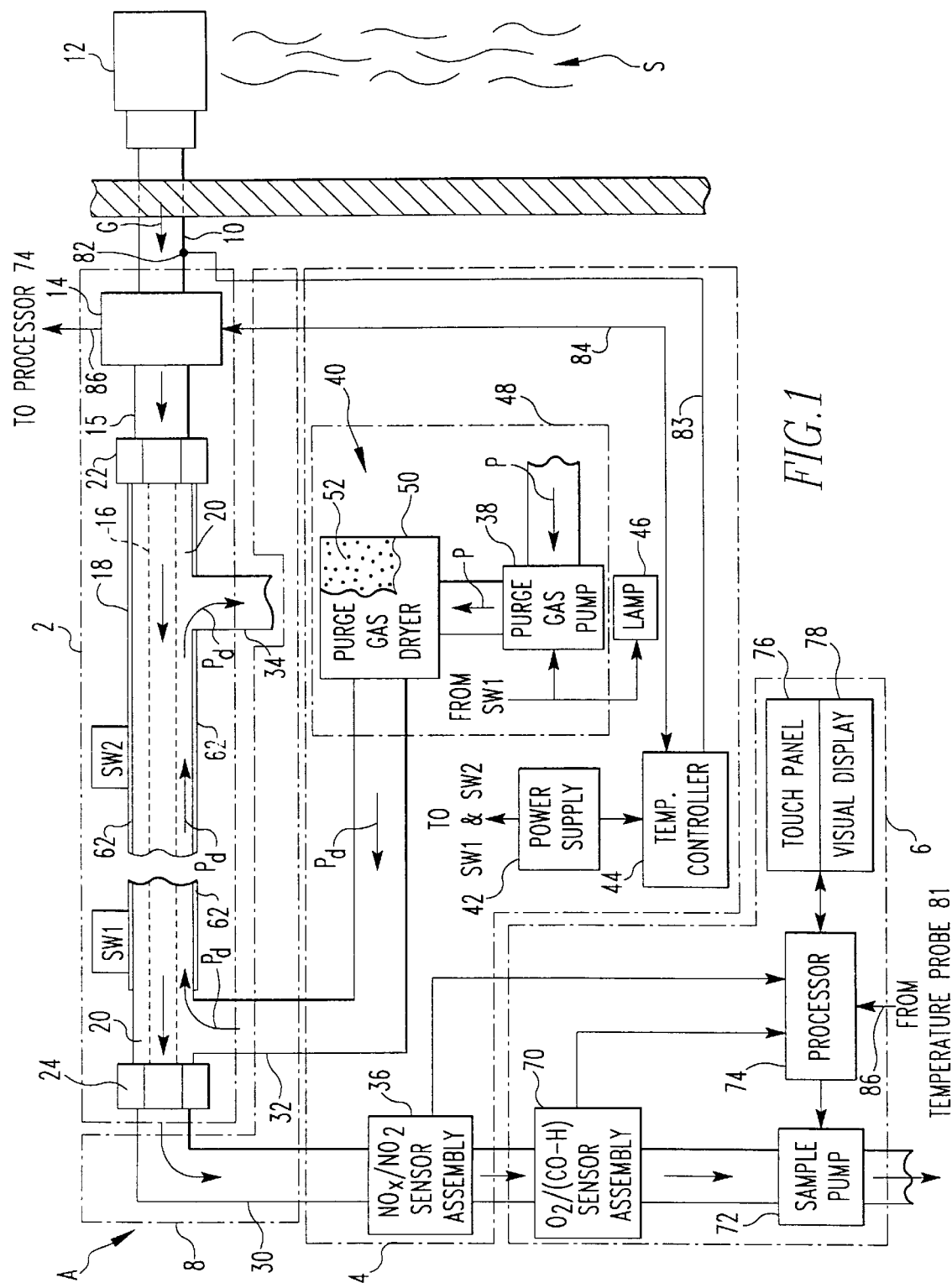
FIG. 1 is a schematic diagram of an apparatus in accordance with the present invention for obtaining a sample of gas from a stream of the products of combustion.

With reference to FIG. 1, an apparatus A for obtaining a sample of gas G from a stream S of products of combustion includes a probe enclosure 2, a power supply enclosure 4 and a combustion analyzer 6. A conduit pipe 8 extends between the probe enclosure 2 and the power supply enclosure 4.

The probe enclosure 2 includes a probe tube 10 extending therefrom. A filter probe tip 12, preferably formed of sintered stainless steel, is connected to an end of the probe tube 10 opposite the probe enclosure 2. The filter probe tip 12 enables the sample of gas G to pass therethrough from the stream S of the products of combustion into the probe tube 10. The probe enclosure 2 includes a fluid-tight manifold 14 which receives an end of the probe tube 10 opposite the filter probe tip 12. A sample dryer tube 16 (shown in phantom) is connected in fluid communication with the probe tube 10 by an interface tube 15 which extends between the sample dryer tube 16 and the manifold 14.

The sample dryer tube 16 is received in a purge gas tube 18 along a lengthwise axis thereof. The sample dryer tube 16 and the purge gas tube 18 define a space 20 therebetween for receiving a dry purge gas $P_d$. Fittings 22 and 24 are connected between the purge gas tube 18 and the sample dryer tube 16 at opposite ends thereof. The fitting 22 is positioned adjacent the manifold 14 and connects the sample dryer tube 16 and the interface tube 15 in fluid communication. The fitting 24 connects the end of the sample dryer tube 16 opposite the manifold 14 and a dry sample gas tube 30 in fluid communication. The fittings 22 and 24 form fluid-tight seals between the sample dryer tube 16, the purge gas tube 18, the interface tube 15 and the dry sample gas tube 30. The fluid-tight seals avoid the sample of gas G, the dry purge gas $P_d$ or ambient air from leaking therethrough.

The sample dryer tube 16 has an outside diameter that is smaller than the inside diameter of the purge gas tube 18. The space 20 defined between the purge gas tube 18 and the sample dryer tube 16 is of sufficient extent to receive the dry purge gas $P_d$ therein. The purge gas tube 18 and the sample dryer tube 16 are preferably positioned coaxially so that the space 20 defines an annular shape. However, the sample dryer tube 16 may be loosely received in the purge gas tube 18 so that the outside diameter of the sample dryer tube 16 and the inside diameter of the purge gas tube 18 are in contact. More specifically, the sample dryer tube 16 is positioned adjacent a side of the purge gas tube 18 so that the space 20 defines a crescent shape.

The space 20 receives the dry purge gas $P_d$ from a purge gas supply tube 32 connected in fluid communication with the space 20 through a wall of the purge gas tube 18 adjacent the fitting 24. The dry purge gas $P_d$ received within the space 20 from the purge gas supply tube 32 is urged (in a manner described hereinafter) toward a purge gas exhaust 34, which is connected in fluid communication with the space 20 through the wall of the purge gas tube 18 adjacent the fitting 22. The purge gas exhaust 34 vents the dry purge gas $P_d$, preferably, to ambient atmosphere.

The power supply enclosure 4 includes an $NO_x/NO_2$ sensor assembly 36, a purge gas pump 38, a purge gas dryer 40, a power supply 42, a temperature controller 44 and a lamp 46. The $NO_x/NO_2$ sensor assembly 36 is connected in fluid communication with the sample dryer tube 16 by the dry sample gas tube 30. The purge gas pump 38 is connected to receive purge gas P, preferably ambient air, therein and is connected to provide a pressurized stream of the purge gas P to the purge gas dryer 40 connected in fluid communication therewith. The purge gas dryer 40 is connected in fluid communication with the space 20 by the purge gas supply tube 32. In operation, a pressurized stream of purge gas P exhausted from the purge gas pump 38 flows through the purge gas dryer 40 which dries the purge gas P to produce the dry purge gas $P_d$ which flows through the purge gas supply tube 32 to the space 20. Alternatively, the positions of the purge gas pump 38 and the purge gas dryer 40 are reversed. The dry purge gas $P_d$ received from the purge gas supply tube 32 flows through the space 20 and is exhausted from the purge gas exhaust 34. The purge gas pump 38 and the purge gas dryer 40 are connected in series and coact to define a source 48 of dry purge gas $P_d$.

The purge gas dryer 40 preferably includes a container 50 having a desiccant 52 received therein. The desiccant 52 removes water vapor from the purge gas P flowing through the container 50 thereby creating the dry purge gas $P_d$. Hence, the dry purge gas $P_d$ flowing into the space 20 contains less water vapor than the purge gas P entering the purge gas dryer 40. Preferably, the dry sample gas tube 30 and the purge gas supply tube 32 are disposed inside the conduit pipe 8 which extends between the probe enclosure 2 and the power supply enclosure 4.

The power supply 42 receives AC power from a source (not shown) and converts the received AC power into electric power utilizable by the temperature controller 44, the purge gas pump 38, the lamp 46 and a purge gas tube heater 62. The purge gas tube heater 62 is preferably positioned adjacent the purge gas tube 18 for heating the dry purge gas $P_d$ received in the space 20 and for heating the sample of gas G received in the sample dryer tube 16. A first temperature sensitive switch SW1 is electrically connected between the power supply 42 and the purge gas pump 38, and the power supply 42 and the lamp 46. A second temperature sensitive switch SW2 is electrically connected between the power supply 42 and the purge gas tube heater 62. The switches SW1 and SW2 are preferably positioned adjacent the purge gas tube heater 62 to detect the temperature thereof.

The combustion analyzer 6 includes an $O_2$/(CO—H) sensor assembly 70, a sample pump 72, a processor 74, a touch panel 76 and a visual display 78. The $O_2$/(CO—H) sensor assembly 70 is connected between the sample pump 72 and the $NO_x/NO_2$ sensor assembly 36 and in fluid communication therewith. The sensor assemblies 36, 70 are each adapted to detect one or more constituents in the sample of gas G and to provide an output that varies in response to the amount of the one or more constituents detected thereby. Preferably, the sensor assembly 36 includes an $NO_x$ sensor and an $NO_2$ sensor (not shown) positioned adjacent each other to detect substantially simultaneously their respective constituents. Similarly, the sensor 70 includes an 02 sensor and an CO—H sensor (not shown) positioned adjacent each other to detect substantially simultaneously their respective constituents. The processor 74 is connected to receive the outputs from the sensor assemblies 36, 70. Moreover, the processor 74 is connected to receive outputs from the touch panel 76 and a temperature probe 81 (shown in FIG. 2) and to provide data and control signals to an input of the visual display 78.

Figure 2:
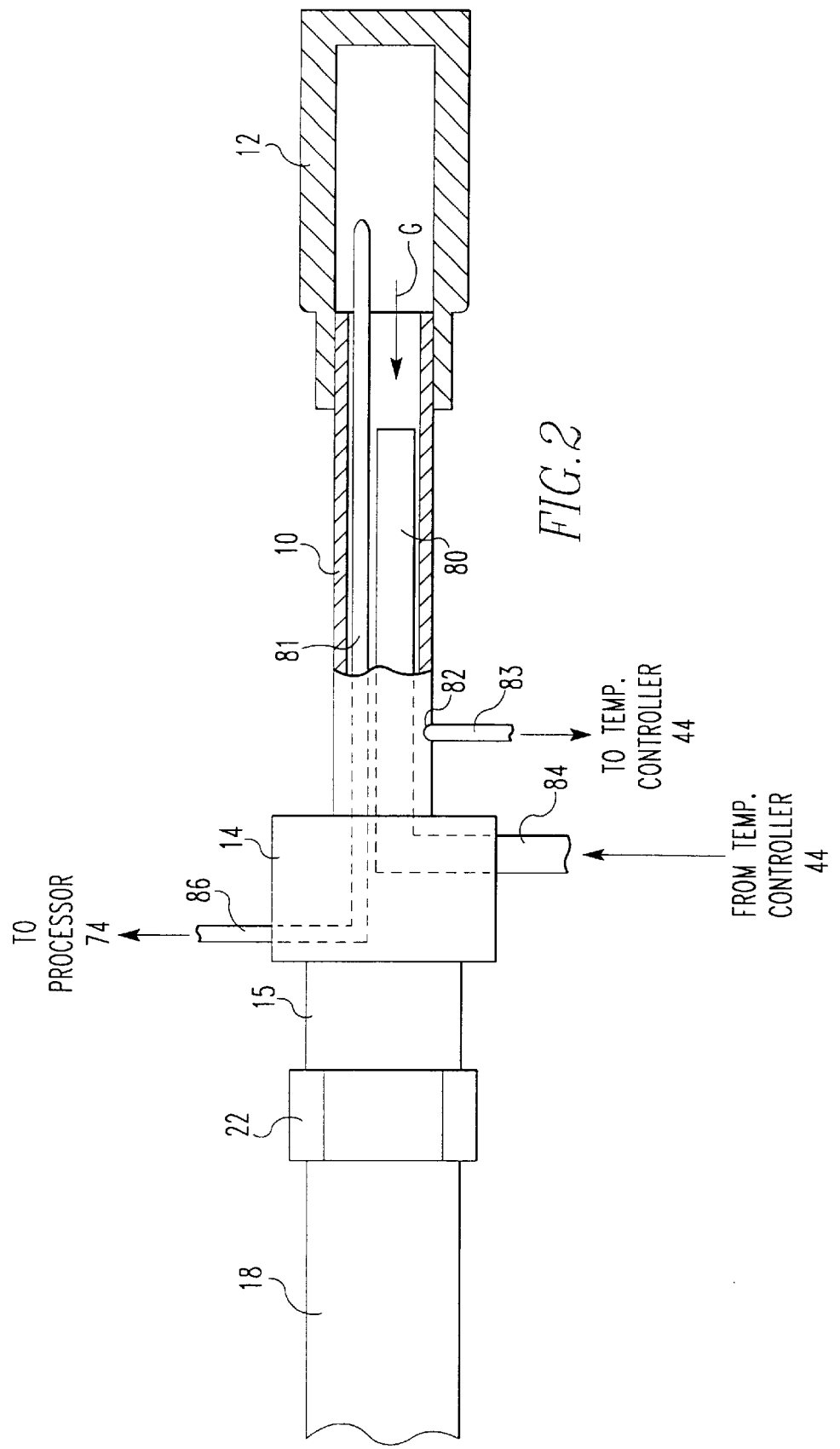
FIG. 2 is an enlarged view, partially cut away, of an end of the apparatus shown in FIG. 1 which receives the sample of gas from the stream of the products of combustion.
Figure 3A:
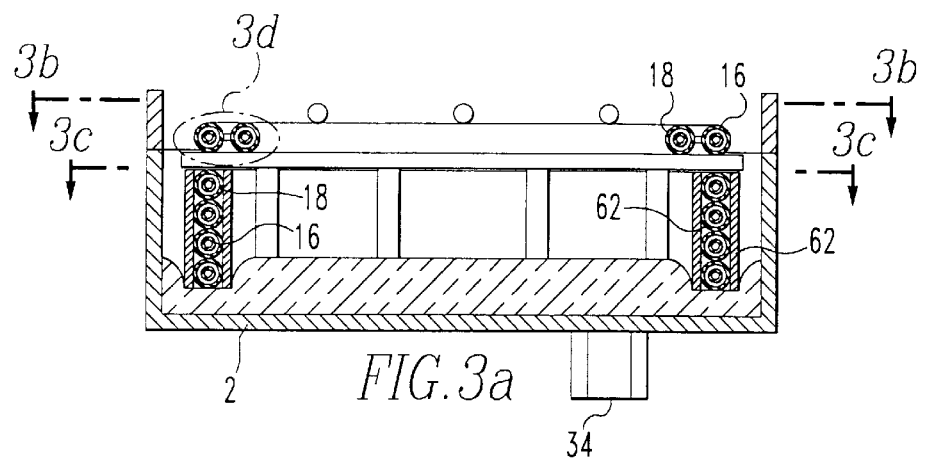
FIGS. 3a–3d are sectional views of a probe enclosure of the apparatus shown in FIG. 1.
Figure 3D:
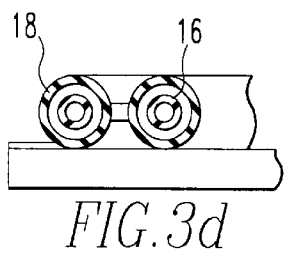
Figure 3B:
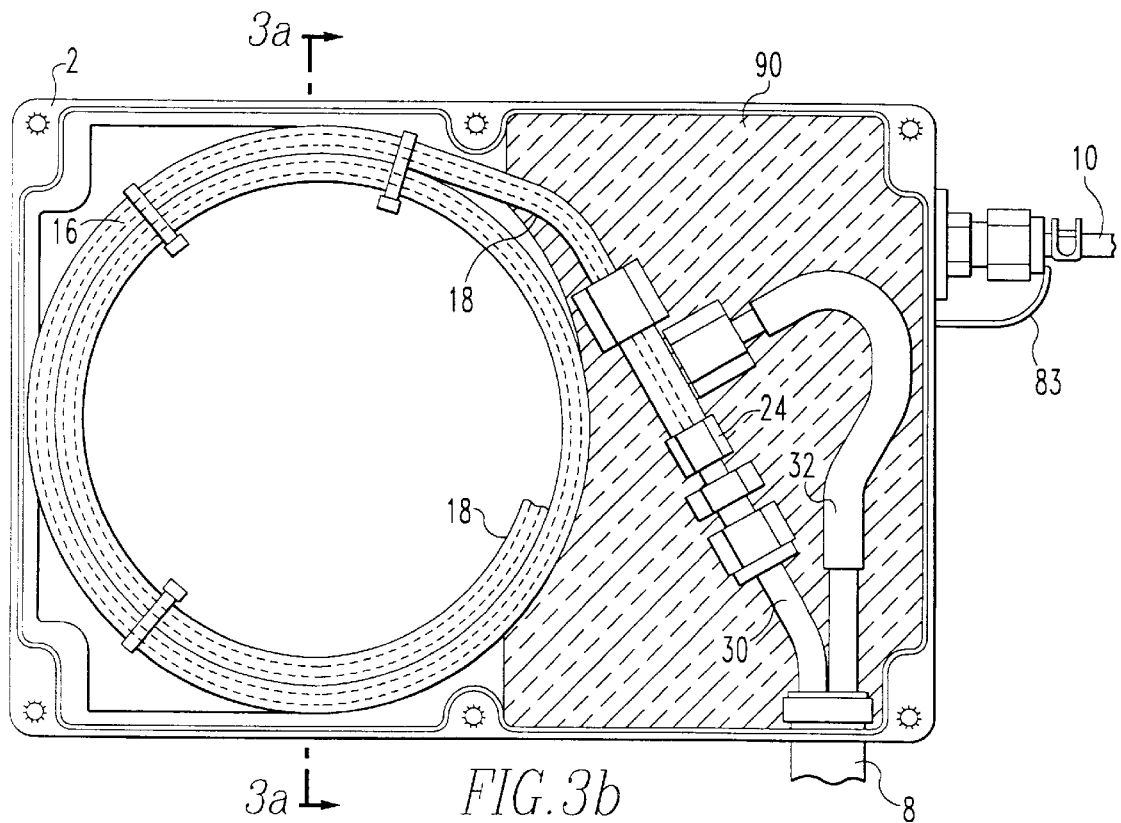
Figure 3C:
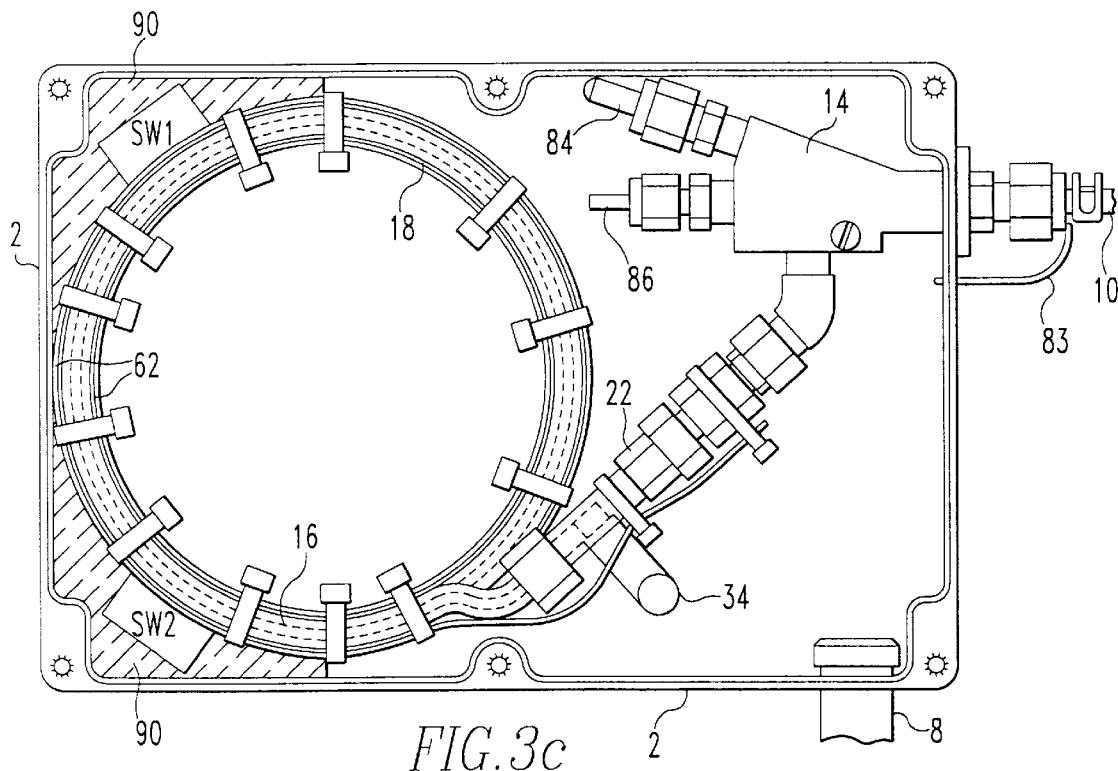

With reference to FIG. 2 and with ongoing reference to FIG. 1, positioned in the probe tube 10 adjacent the filter probe tip 12 are a probe tube heater 80 which is utilized to maintain the temperature of the sample of gas G above a dew point temperature of water vapor therein and the temperature probe 81 which detects the temperature of the sample of gas G received in the filter probe tip 12. A temperature probe 82 is positioned on the probe tube 10 adjacent an end thereof opposite the filter probe tip 12 for detecting the temperature of the probe tube 10 adjacent the probe enclosure 2. The temperature controller 44 has an output connected to the probe tube heater 80 by one or more conductors 84 and an input connected to an output of the temperature probe 82 by one or more conductors 83. The output of the temperature probe 81 is connected to an input of the processor 74 by one or more conductors 86. The output of the temperature probe 82 varies as a function of the temperature detected thereby. When the output of the temperature probe 82 sensed by the temperature controller 44 is below a set-point temperature thereof, the temperature controller 44 causes electrical energy to be supplied to the probe tube heater 80. In response to the supply of electrical energy, the probe tube heater 80 increases in temperature thereby heating the probe tube 10 and, hence, the sample of gas G received therein. The probe tube heater 80, the temperature probe 82 and the temperature controller 44 coact to maintain the temperature of the probe tube 10, and hence the temperature sample of gas G received in the probe tube 10, at or above the set-point temperature of the temperature controller 44. Preferably, the set-point temperature of the temperature controller 44 is above the dew point temperature of water in the sample of gas G, e.g. 140° F.

The manifold 14 enables the temperature controller 44 and the processor 72 to be connected to the probe tube heater 80 and the temperature probe 81 by the conductors 84 and 86, respectively, while maintaining a fluid-tight connection between the probe tube 10 and the interface tube 15.

With reference to FIGS. 3a–3d, and with ongoing reference to FIGS. 1 and 2, the purge gas tube 18 having the sample dryer tube 16 received therein is preferably coiled inside the probe enclosure 2. The fittings 22 and 24 are disposed at opposite ends of the purge gas tube 18 and the sample dryer tube 16, which are approximately 8 feet in length. The purge gas tube heater 62 is positioned to heat the purge gas tube 18 and the sample dryer tube 16 adjacent the fitting 22. More specifically, the purge gas tube heater 62 is positioned to heat approximately 5 feet of the purge gas tube 18 and the sample dryer tube 16 adjacent the fitting 22, thus leaving unheated the 3 feet of purge gas tube 18 and sample dryer tube 16 adjacent fitting 24.

The switches SW1 and SW2 are preferably temperature sensitive switches, of a type known in the art, which switch state as a function of the temperature detected thereby relative to a set-point temperature thereof. The probe enclosure 2 includes insulation 90 therein and a cover (not shown) positionable on a side of the probe enclosure 2 opposite the purge gas exhaust 34. The probe enclosure 2, cover and insulation 90 coact to maintain the purge gas tube 18 and the sample dryer tube 16 heated by the purge gas tube heater 62 at or near a set-point temperature of the second switch SW2, preferably 150°–160° F. More specifically, the probe enclosure 2, cover and insulation 90 coact to avoid exposure of the purge gas tube 18 and the sample dryer tube 16 to ambient atmosphere which can cause the temperature thereof to decrease below the set-point temperature of the second switch SW2 and/or cause temperature gradients along the portion of the purge gas tube 18 and the sample dryer tube 16 heated by purge gas tube heater 62. Preferably, the probe tube heater 80 and the purge gas tube heater 62 heat the sample of gas G to a temperature greater than the dew point temperature of water vapor therein.

Figure 4:
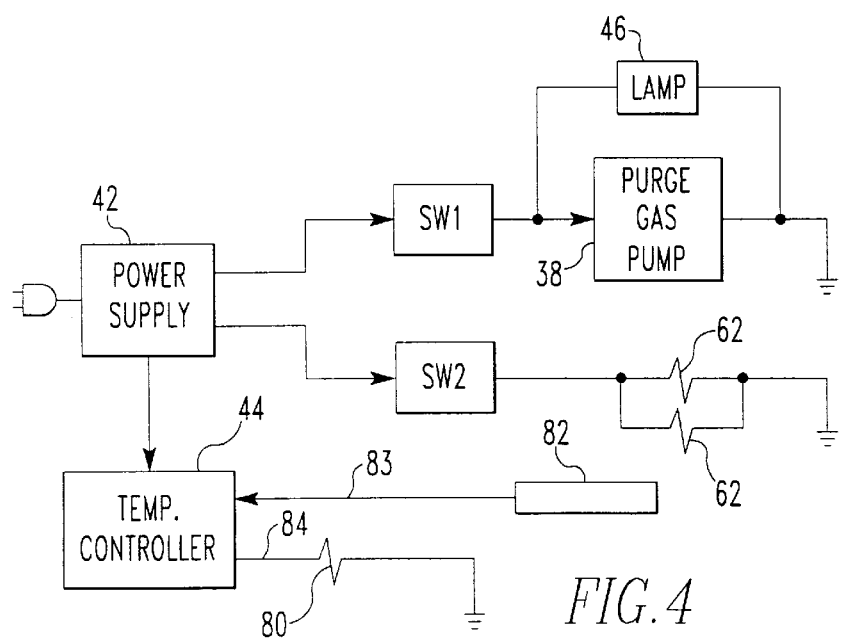
FIG. 4 is an electrical diagram of components of the probe enclosure and a power supply enclosure of the apparatus shown in FIG. 1.

With reference to FIG. 4, and with ongoing reference to FIG. 1, the power supply 42 supplies power to the purge gas pump 38 and the lamp 46 via the first switch SW1. The first switch SW1 is connected so that at temperatures at or above a set-point temperature thereof, e.g., 140° F., the first switch SW1 forms a conductive path between the power supply 42 and the purge gas pump 38, and the power supply 42 and the lamp 46. At temperatures below the set-point temperature, however, the first switch SW1 electrically isolates the purge gas pump 38 and the lamp 46 from the power supply 42. Hence, at temperatures at or above the set-point temperature of the first switch SW1, the purge gas pump 38 is running and the lamp 46 is illuminated, and at temperatures below the set-point temperature of the first switch SW1, the purge gas pump 38 is inactive and the lamp 46 is extinguished.

The power supply 42 also provides power to the purge gas tube heater 62, shown schematically as resistors in FIG. 4, through the second switch SW2. The second switch SW2 is connected so that at temperatures below the set-point temperature thereof, e.g., 150°–160° F., the second switch SW2 forms a conductive path between the power supply 42 and the purge gas tube heater 62. When the temperature detected by the second switch SW2 equals or exceeds the set-point temperature thereof, however, the second switch SW2 electrically isolates the purge gas tube heater 62 from the power supply 42. Hence, at temperatures below the set-point temperature of the second switch SW2, the purge gas tube heater 62 supplies heat to the purge gas tube 18 and the sample dryer tube 16, and at temperatures at or above the set-point temperature of the second switch SW2, the purge gas tube heater 62 withholds heat from the purge gas tube 18 and the sample dryer tube 16.

The power supply 42 also provides power to the temperature controller 44 which may be a proportional, integral and/or derivative type controller or may be a simple ON/OFF type controller.

With ongoing reference to FIG. 1, in use of the apparatus A beginning from ambient temperature, the power supply 42 is connected to a source of AC power which causes the power supply 42 to supply electric power to the purge gas tube heater 62 via the second switch SW2. In response to the supply of electric power, the purge gas tube heater 62 increases in temperature thereby increasing the temperatures of the purge gas tube 18 and the sample dryer tube 16. The power supply 42 also supplies electric power to the temperature controller 44 which, in response, monitors the output of the temperature probe 82 indicative of the temperature detected thereby. In response to detecting the output of the temperature probe 82, the temperature controller 44 controllably supplies electric power to the probe tube heater 80 until the temperature detected by the temperature probe 82 reaches the set-point temperature established at the temperature controller 44. Preferably, the temperature controller 44, the probe tube heater 80 and the temperature probe 82 coact to maintain the temperature of the probe tube 10 above the dew point temperature of water in the sample of gas G.

When the temperature detected by the first switch SW1 reaches the set-point temperature thereof, the first switch SW1 changes state thereby forming a conductive path between the power supply 42 and the purge gas pump 38, and the power supply 42 and the lamp 46. In response to the first switch SW1 forming the conductive path, the lamp 46 is illuminated and the purge gas pump 38 begins running thereby obtaining the purge gas P, e.g., ambient air, from a source thereof and urging the purge gas P through the desiccant 52 disposed in the container 50 of the purge gas dryer 40. The desiccant 52 removes water vapor from the purge gas P thereby producing the dry purge gas $P_d$ which is urged through the purge gas supply tube 32 and into the space 20.

Preferably, the purge gas tube heater 62 and the probe tube heater 80 are operated for a suitable warmup interval, e.g., 15 minutes, prior to obtaining the sample of gas G from the stream S of the products of combustion. This warmup interval enables the temperature of the purge gas tube 18, the sample dryer tube 16, the probe tube 10 and the filter probe tip 12 to stabilize at a temperature above the dew point temperature of water vapor in the sample of gas G. After the warmup interval and when the lamp 46 is illuminated, a start sample command is entered in the touch panel 76 and communicated to the processor 74 which causes electric power to be supplied to the sample pump 72. In response to the supply of electric power, the sample pump 72 begins running thereby causing the sample of gas G to be extracted from the stream S of the products of combustion. The sample pump 72 draws the sample of gas G extracted from the stream S of the products of combustion through the filter probe tip 12, the probe tube 10, the interface tube 15, the sample dryer tube 16, the dry sample gas tube 30 and to the sensor assemblies 36, 70. The sensor assemblies 36, 70 each detect one or more constituents in the sample of gas G, such as, for example, $NO_2$, NO, $O_2$ or CO—H, and provide to the processor 74 outputs indicative of the detected one or more constituents. The processor 74 utilizes the outputs of the sensor assemblies 36, 70 and the temperature detected by temperature probe 81 to determine numeric values of the detected constituents and causes the numeric values to be displayed on the visual display 78.

With ongoing reference to FIG. 1, the dry purge gas $P_d$ in the space 20 flows from the purge gas supply tube 32 to the purge gas exhaust 34 in a direction opposite the flow of the sample of gas G in the sample dryer tube 16. The sample dryer tube 16 is formed at least in part from a hydrophilic membrane, preferably a perfluorocarbon sulfonic acid membrane, which selectively enables water vapor to be conveyed therethrough. Such membranes are produced by E.I. duPont de Nemours & Co., Inc., Wilmington, Del., and sold under the trademark NAFION® membranes. Similar perfluorocarbon sulfonic acid membranes are produced by Dow Chemical Company and others.

Because the desiccant 52 removes from the purge gas P the water vapor therein, the dry purge gas $P_d$ entering the space 20 contains less water vapor than the sample of gas G flowing in the sample dryer tube 16. The hydrophilic membrane forming at least part of the sample dryer tube 16 enables water vapor in the sample of gas G flowing in the sample dryer tube 16 to be conveyed to the dry purge gas $P_d$ flowing in the space 20. Maintaining the temperature of the purge gas tube 18 and the sample dryer tube 16, and, hence, the temperatures of the sample of gas G and the dry purge gas $P_d$, at or above the dew point temperature of water vapor therein, enhances the conveyance of water vapor from the sample of gas G to the dry purge gas $P_d$.

The sensor assemblies 36, 70 are each adapted to sense one or more specific constituents in the sample of gas G at or near ambient temperature. Accordingly, the purge gas tube 18 and the sample dryer tube 16 adjacent the fitting 24 are unheated. Similarly, the dry sample gas tube 30 is unheated. The sample of gas G passing through the dry sample gas tube 30 and the sample dryer tube 16 adjacent the fitting 24 releases heat therethrough so that the temperature of the sample of gas G at the sensor assemblies 36, 70 is within a desired range of operating temperatures thereof.

In accordance with the present invention, the sample of gas G exhausted from the sample dryer tube 16 contains significantly less water vapor than the sample of gas entering the sample dryer tube 16, and the dry purge gas Pd exhausted from the space 20 contains more water vapor than the dry purge gas $P_d$ entering the space 20. Moreover, the desiccant 52 in the purge gas dryer 40 removes water vapor from the purge gas P so that the dry purge gas $P_d$ entering the space 20 contains less water vapor than the purge gas P entering the purge gas dryer 40.

Preferably, the sample of gas G exhausted from the sample dryer tube 16 has a dew point temperature below 50° F. and the flow rate of the dry purge gas $P_d$ in the space 20 is at least two times, and preferably four times, the flow rate of the sample of gas G in the sample dryer tube 16. More preferably, the flow rate of the dry purge gas $P_d$ is greater than the product of the flow rate of the sample of gas G and the percentage of water vapor in the sample of gas G divided by the dew point moisture capacity of the dry purge gas $P_d$.

Figure 5A:
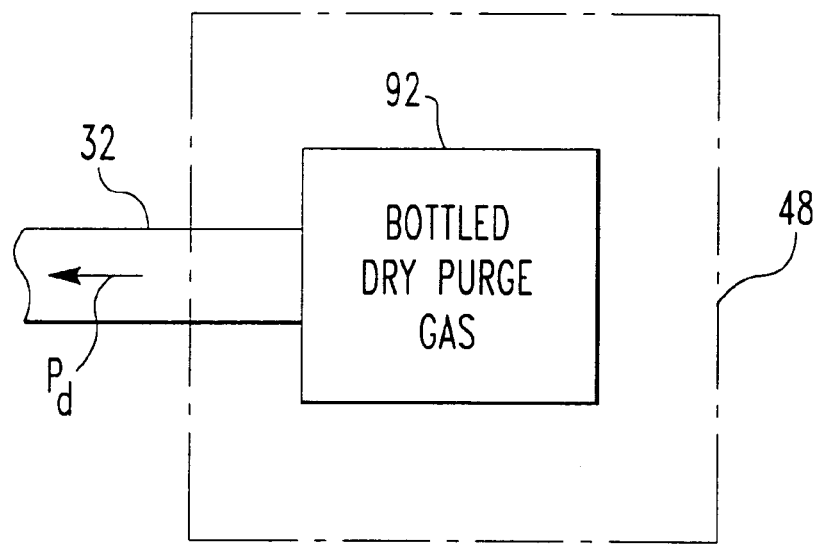
FIGS. 5a and 5b are alternate embodiments of sources of purge gas for the apparatus shown in FIG. 1.
Figure 5B:
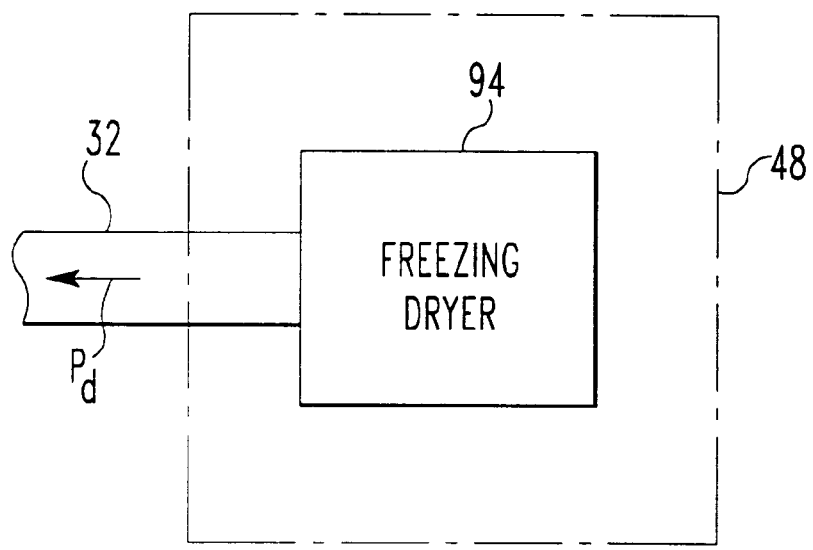

With reference to FIGS. 5a and 5b, the source 48 of dry purge gas $P_d$ in FIG. 1 includes the purge pump 38 and the purge gas dryer 40. Alternatively, the source 48 of dry purge gas $P_d$ can include bottled dry purge gas 92, a freezing dryer 94, or the like, which can supply the stream dry purge gas $P_d$ to the purge gas supply tube 32 and the space 20.

The invention has been described with reference to the preferred embodiment. Obvious modifications and alterations will occur to others upon reading and understanding the preceding detailed description. For example, while the embodiment shown in FIG. 1 has sensor assemblies 36, 70, only one sensor can be utilized, or sensor assemblies (not shown) can be provided in addition to sensor assemblies 36, 70. Moreover, temperature controller 44 can detect a resistance of the probe tube heater 80 and cause electrical power to be supplied to the probe tube heater as a function of the detected temperature. In this manner, one or both of the temperature probes 81, 82 can be eliminated. It is intended that the invention be construed as including all such modifications and alterations insofar as they come within the scope of the appended claims or the equivalents thereof.

We claim:

1. A method of sampling gas obtained from a stream of products of combustion, the method comprising the steps of:
   (a) obtaining a sample of gas from a stream of products of combustion;
   (b) urging the sample of gas through a sample dryer tube disposed inside a purge gas tube;
   (c) urging a purge gas through a space formed between the purge gas tube and the sample dryer tube in a direction opposite the sample of gas in the sample dryer tube;
   (d) maintaining the sample dryer tube adjacent an end thereof which receives the sample of gas therein one of at and above a temperature above the dew point temperature of water in the sample of gas; and
   (e) sensing a constituent in the sample of gas exhausted from the sample dryer tube, wherein:
   the purge gas entering the space contains less water vapor than the sample of gas entering the sample dryer tube; and
   the sample dryer tube is formed at least in part from a hydrophilic membrane which enables water vapor to be conveyed from the sample of gas to the purge gas whereby the purge gas exhausted from the sample dryer tube contains more water vapor than the purge gas entering the space, and the sample of gas exhausted from the space contains less water vapor than the sample of gas entering the sample dryer tube.

2. The method as set forth in claim 1, further including the step of:
   (f) maintaining in advance of entering the sample dryer tube a temperature of the sample of gas above the dew point temperature of water therein.

3. The method as set forth in claim 1, further including the step of displaying an amount of the sensed constituent in the sample of gas.

4. The method as set forth in claim 1, wherein step (d) includes the steps of:
   heating the sample dryer tube adjacent the end thereof that receives the sample of gas therein; and
   withholding heat from the end of the sample dryer tube adjacent the end thereof where the sample of gas is exhausted.

5. An apparatus for sampling gas obtained from a stream of products of combustion, the apparatus comprising:
   a probe tube having a tip positionable in the stream of products of combustion;
   a sample dryer tube connected in fluid communication with an end of the probe tube opposite the tip;
   a purge gas tube having the sample dryer tube received therein along a lengthwise axis of the purge gas tube, the purge gas tube and the sample dryer tube defining a space therebetween;
   a source of purge gas which urges a purge gas through the space in a first direction;
   a sample pump which urges through the sample dryer tube in a second direction opposite the first direction a sample of gas obtained from the stream of products of combustion via the probe tube; and
   a sensor which detects a constituent in the sample of gas exhausted from the sample dryer tube, wherein:
   the purge gas entering the space contains less water vapor than the sample of gas;
   the sample dryer tube is formed at least in part of a hydrophilic membrane; and
   water vapor contained in the sample of gas is conveyed through the hydrophilic membrane part of the sample dryer tube to the purge gas flowing in the space so that the purge gas exhausted from the space contains more water vapor than the purge gas entering the space and the sample of gas exhausted from the sample dryer tube contains less water vapor than the sample of gas entering the sample dryer tube.

6. The apparatus as set forth in claim 5, further including a probe tube heater for maintaining the temperature of the sample of gas received in the probe tube above the dew point temperature of water vapor therein.

7. The apparatus as set forth in claim 6, further including:
   a temperature probe positioned on the probe tube for detecting a temperature thereof, the temperature probe having an output that varies as a function of the detected temperature; and
   a temperature controller having an input connected to the temperature probe for detecting the output thereof and an output connected to the probe tube heater, wherein:
   the temperature controller causes electrical power to be supplied to the probe tube heater as a function of the output of the temperature probe detected by the temperature controller.

8. The apparatus as set forth in claim 6, wherein a temperature controller detects a resistance of the probe tube heater and causes electrical power to be supplied to the probe tube heater as a function of the detected resistance.

9. The apparatus as set forth in claim 5, further including a purge gas tube heater positioned adjacent the purge gas tube for maintaining the temperature of the sample of gas received in the sample dryer tube above the dew point temperature of water vapor in the sample of gas.

10. The apparatus as set forth in claim 9, further including a temperature controlled switch electrically connected between the purge gas tube heater and a source of electrical power and positioned to detect the temperature of the purge gas tube heater, wherein:
   the temperature controlled switch causes electrical power to be supplied from the source of electrical power to the purge gas tube heater as a function of the temperature detected thereby.

11. The apparatus as set forth in claim 5, wherein the source of purge gas includes one of:
   (i) a dryer and a purge gas pump connected in series with the space, the dryer removing water vapor from the purge gas;
   (ii) a bottle of dry purge gas; and
   (iii) a freezing dryer.

12. The apparatus as set forth in claim 11, wherein the dryer connected in series with the purge gas pump includes:
   a container; and
   a desiccant received in the container, wherein:
   the purge gas pump urges the purge gas through the desiccant which removes water vapor from the purge gas.

13. The apparatus as set forth in claim 12, wherein the purge gas is ambient air.

14. The apparatus as set forth in claim 5, further including:
   a visual display; and
   a processor connected to receive an output of the sensor and connected to an input of the visual display, wherein:

the sensor has an output that varies as a function of the amount of the constituent detected thereby; and the processor causes the visual display to display data corresponding to the output of the sensor detected by the processor.

15. The apparatus as set forth in claim 5 wherein the sample of gas exhausted from the sample dryer tube has a dew point temperature below 50° F.

16. The apparatus as set forth in claim 5, wherein the flow rate of the purge gas is one of:

(i) at least twice the flow rate of the sample of gas; and (ii) greater than a product of the flow rate of the sample of gas and the percent of water vapor in the sample of gas divided by the dew point moisture capacity of the purge gas.

17. The apparatus as set forth in claim 5, wherein the hydrophilic membrane is a perfluorocarbon sulfonic acid membrane.

18. A gas sampling apparatus comprising:

a source of dry purge gas;

a sample dryer tube positioned inside a purge gas tube, the purge gas tube and the sample dryer tube defining a space therebetween for receiving a stream of dry purge gas from the source of dry purge gas;

a sample pump connected to obtain a sample of gas from a stream of products of combustion and to cause the obtained sample of gas to flow through the sample dryer tube; and a heater for maintaining a temperature of the sample of gas entering the sample dryer tube one of at and above a dew point temperature of water in the sample of gas, wherein:

the stream of dry purge gas in the space flows in a direction opposite the sample of gas in the sample dryer tube;

the purge gas entering the purge gas tube contains less water vapor than the sample of gas; and the sample dryer tube is formed at least in part of a hydrophilic membrane that enables water vapor contained in the sample of gas to be conveyed therethrough to the stream of dry purge gas thereby reducing the amount of water vapor in the sample of gas.

19. The gas sampling apparatus as set forth in claim 18, wherein the source of dry purge gas includes one of:

(i) a purge gas pump and a dryer connected in series with the space, wherein the purge gas pump produces a stream of purge gas, the dryer includes a container having a desiccant received therein and the stream of purge gas is passed through the desiccant received in the container thereby producing the dry purge gas;

(ii) a bottle of dry purge gas; and (iii) a freezing dryer.

20. The gas sampling apparatus as set forth in claim 18, wherein:

the heater is positioned to heat a first part of the sample dryer tube adjacent the end thereof which receives the sample of gas; and a second part of the sample dryer tube opposite the first part is unheated.

\* \* \* \* \*

UNITED STATES PATENT AND TRADEMARK OFFICE
CERTIFICATE OF CORRECTION

PATENT NO.  : 6,042,634
DATED       : March 28, 2000
INVENTOR(S) : Robert H. Spitzer It is certified that error appears in the above-identified patent and that said Letters Patent is hereby corrected as shown below:

Column 5 Line 21 "02 sensor" should read --$O_2$ sensor--.

Column 8 Line 35 "Pd" should read --$P_d$--.

Signed and Sealed this

Twenty-seventh Day of February, 2001

Attest:

NICHOLAS P. GODICI

Attesting Officer    Acting Director of the United States Patent and Trademark Office